United States Patent [19]

Kovar et al.

[11] Patent Number: 5,882,939
[45] Date of Patent: Mar. 16, 1999

[54] SEPARATING MATERIALS FOR LINKING TLC AND FTIR

[75] Inventors: Karl Artur Kovar, Tübingen; Walter Fischer, Griesheim; Heinz Emil Hauck, Gross-Umstadt, all of Germany

[73] Assignee: Merck Patent Gesellschaft mit Beschrankter Haftung, Germany

[21] Appl. No.: 913,469

[22] PCT Filed: Mar. 7, 1996

[86] PCT No.: PCT/EP96/00965

§ 371 Date: Sep. 18, 1997

§ 102(e) Date: Sep. 18, 1997

[87] PCT Pub. No.: WO96/29596

PCT Pub. Date: Sep. 26, 1996

[30] Foreign Application Priority Data

Mar. 18, 1995 [DE] Germany ......... 195 09 949.4

[51] Int. Cl.$^6$ ................................ G01N 30/90
[52] U.S. Cl. ............ 436/162; 73/61.54; 210/198.3; 422/56; 422/70; 422/82.05; 422/82.09; 436/164; 436/169; 436/178
[58] Field of Search .................. 436/162, 164, 436/169, 178; 422/70, 82.05, 82.09, 56, 57; 210/198.3; 73/61.54

[56] References Cited

U.S. PATENT DOCUMENTS 4,271,021 6/1981 Hauck .................. 210/198.3

OTHER PUBLICATIONS

Chemical Abstracts CA 117: 123754 Danielson et al., Anal. Chem. (1992), 64(18), 2183–6, 1992.

Chemical Abstracts CA 113: 178964 Yoshioka et al., J. Chromatogr. (1990), 515, 205–12, 1990.

Miller, Chromatography: Concepts and Contrasts. John Wiley & Sons New York: 1988, pp. 236–239.

Primary Examiner—Jan Ludlow
Attorney, Agent, or Firm—Millen, White, Zelano, & Branigan, P.C.

[57] ABSTRACT

The invention concerns separating materials for thin-layer chromatography, the materials having a sorbent layer formed from sorbent particles and disposed on a carrier. A reflection intensifier, preferably magnesium tungstate and/or $Bi_2O_3$, is added to the sorbent layer. This addition comprises at least 10 wt % relative to the amount of sorbent. In preferred embodiments, the particle size of the reflection intensifier is 3 to 5 $\mu$m and the amount of the reflection intensifier is 0.6 to 15 times the amount of sorbent. These separating materials are particularly suitable for the in-situ measurement of FTIR spectra. The invention also concerns the use of these separating materials for the in-situ measurement of FTIR spectra.

10 Claims, 1 Drawing Sheet

SEPARATING MATERIALS FOR LINKING TLC AND FTIR

The invention relates to separating materials for thin-layer chromatography (TLC) which are suitable, in particular, for in situ infrared spectroscopy (IR) and Fourier transform infrared spectroscopy (FTIR).

For some time now research has been carried out on linking TLC to infrared spectroscopy, the objective being to combine TLC, a powerful and economical separation method, with IR, a spectroscopic method acknowledged as being informative (Percival C. J., Griffiths P. R. (1975), Anal. Chem., 45 (1), pp. 154–156). Despite the major effort in fabricating special layers (e.g. silver chloride as the base, with an addition of the perfluorinated hydrocarbon fluorolube to reduce scattering) the detection limit and sensitivity remained inadequate. Moreover, if silica gel was used as the stationary phase, the spectral range important for analytical purposes and known as the "fingerprint range" could not be used, owing to the intrinsic absorption of the silica gel.

Owing to its silanol and siloxane groups, silica gel is one of the strongly absorbing materials. Reflectance spectroscopy with such strongly absorbing materials involves an anomalous profile of the dispersion curve, most of the incident radiation being reflected directionally. This leads to so-called "residual rays" which no longer contain any spectral information. Further problems arise from the fact that the effective penetration depth in the vicinity of absorption bands of the matrix is much less than in spectral ranges without matrix absorption. Instead of silica gel, Danielson et al. (1992) Analyt. Chem. 64, 2183–2186, therefore employed zirconium oxide as the sorbent. While it was possible to measure FTIR spectra of substances adsorbed on this sorbent, many substances which can be separated without any problems on silica gel were impossible to separate on zirconium oxide, since they either remained in the start zone or migrated with the solvent front. This meant that the analytically important range of $R_f$ values between 0.2 and 0.8 could not be attained.

In the wave number range between 1350 and 1000 the strong intrinsic absorption of the silica gel in this range produces a strong interfering band which is superimposed on the DRIFT spectra (diffuse reflectance infrared Fourier transform; reflectance spectra in the medium-infrared range) of adsorbed substances. Consequently, significant portions of the "fingerprint range" can no longer be covered. DRIFT measurements on silica gel layers were first carried out by Fuller and Griffiths (Fuller M. P., Griffiths P. R. (1978), Anal. Chem. 50 (13), pp. 1906–1910; and Fuller M. P., Griffiths P. R. (1980) Appl. Spectrosc., 1980 (34), pp. 533–539). In so doing, spectra of methylene blue could be measured with 1.2 $\mu$g of substance.

Given the versatility of the possible applications, in particular of silica gel 60 (pore size 60 Angstroms) as a sorbent in TLC and HPTLC and the quality standard achieved, in particular, for this stationary phase there is a need for the development of suitable precoated layers on the basis of silica gel for linking with IR spectroscopy. It is an object of the invention to provide separating materials for thin-layer chromatography which permit an in situ study by means of FTIR spectroscopy even with small amounts of sample material. This object is achieved by the provision of separating materials for thin-layer chromatography, whose sorbent layer comprises an addition of a reflection enhancer.

The invention relates to separating materials for thin-layer chromatography which comprise a sorbent layer, formed from sorbent particles, on a support, the sorbent layer comprising an addition of at least 10 percent by weight, based on the amount of sorbent, of a reflection enhancer, preferably magnesium tungstate and/or $Bi_2O_3$. In preferred embodiments the particle size of the reflection enhancer is 3–5 $\mu$m and the amount of the reflection enhancer is from 0.6 to 1.5 times the amount of sorbent. $SiO_2$-containing sorbent particles are preferred.

The invention further relates to the use of this separating material for separation methods followed by in situ measurement of an FTIR spectrum.

Reflection enhancers suitable according to the invention have good reflectance in the IR. Such materials are known in principle. They include metals, insofar as they are resistant to the eluents customary in thin-layer chromatography, and oxygen-containing metal compounds. In particular, according to the invention preference is given to magnesium tungstate and $Bi_2O_3$ as reflection enhancers. According to the invention it is also possible for a plurality of substances in mixed form to be added as reflection enhancers. These also include compounds, e.g. magnesium tungstate, which were added as a fluorescent indicator in small amounts (about 2 percent by weight) to the known sorbent layers. According to the invention, however, the reflection enhancer content is more than 10 percent by weight, based on the amount of sorbent.

The addition, according to the invention, of a reflection enhancer to the sorbent layer of silica gel preserves the good chromatographic properties of the sorbent; nevertheless, the signal-to-noise ratio (e.g. in recording a Gram-Schmidt chromatogram, which involves summation over the entire IR spectral range) and the quality of the DRIFT spectra are improved. This improvement in the IR spectroscopic characteristics is also manifested, for example, by the disappearance of the interfering band at wave number 1337.

The grain size and grain size distribution of the reflection enhancers used according to the invention is in the same order of magnitude as the sorbent particles used in TLC or HPTLC. Preferably the grain size of the reflection enhancers is in the range of about 2–20 $\mu$m, in particular of about 3–5 $\mu$m.

The quantitative proportion of the reflection enhancer in the sorbent layer is more than 10 percent by weight, preferably from 0.1 to 9 times, particularly preferably from 0.6 to 1.5 times the amount of sorbent.

Sorbents to be considered include the sorbents customarily used in thin-layer chromatography, in particular silica gel and derivatized silica gels. A large number of derivatized sorbents are known to those skilled in the art and are mentioned in standard publications. These include, in particular, the hydrophobic reversed phase materials known as $C_2$, $C_8$ and $C_{18}$, and hydrophilic materials modified with amino, cyano or diol groups.

As a further addition the sorbent layer may also comprise fluorescent indicators customarily used in thin-layer chromatography. Sorbents and fluorescent indicators are known to those skilled in the art.

Separating materials for thin-layer chromatography normally additionally comprise binders. Binders suitable in principle and their proportions in the sorbent layer are known to those skilled in the art. Inasmuch as binders are used for the novel separating materials, particular preference is given to poly(meth)acrylic acid and poly(meth)acrylates. Particularly preferred binders have mean molecular weights of 3–4 million and are commercially available.

The sorbent particles of the novel separating materials may be of both irregular and regular shape and in particular may be spherical.

The support used for the separating layer can take the form of the glass plates or films customarily used in TLC or HPTLC, but also surface-treated supports, e.g. roughened supports, mirrored supports and/or supports metallized by vapor deposition.

The layer thickness of the sorbent layer of the novel separating materials corresponds to the layer thicknesses customary in TLC and HPTLC. Layer thicknesses of between 30 and 250 µm, in particular between 50 and 140 µm, are preferred according to the invention.

Figure 1:
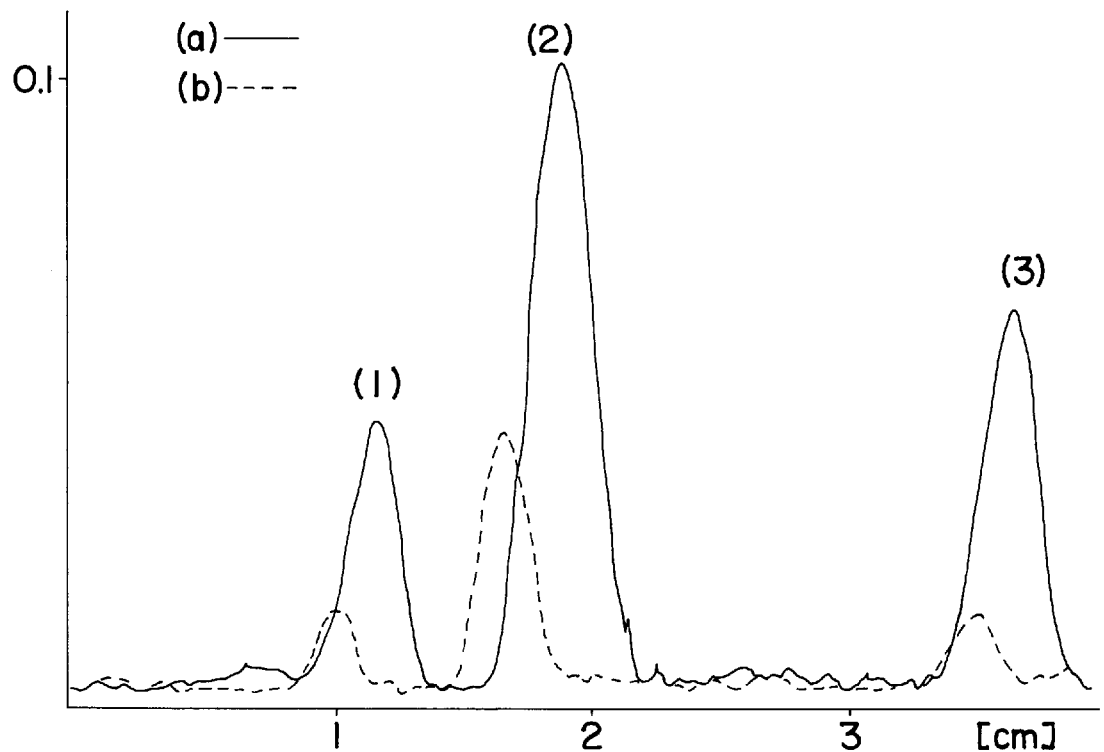
FIG. 1 shows Gram-Schmidt chromatograms of phenazone, caffeine and paracetamol on a sorbent layer according to the invention, comprising 50% by weight of $Bi_2O_3$, compared with a layer without reflection enhancer.

Details on both figures can be found in Example 2.

FTIR spectrometers are commercially available. The in situ measurement of samples separated by thin-layer chromatography typically makes use of an external TLC/HPTLC DRIFT unit. Such units are likewise commercially available; for example, given a fixed measuring beam the thin-layer support is moved on a stage with X and Y movements by means of step motors. The measuring setup is typically purged with dried, $CO_2$-free air. Control of the movement and data acquisition, and processing of the measurement data are carried out by a computer, with the option, if required, of background spectra being measured on an empty point of the thin-layer plate and being subtracted in the course of data processing. Suitable computers are commercially available, as are control and evaluation programs.

EXAMPLE

The following examples are intended to illustrate the subject matter of the invention without limiting the inventive idea.

Example 1

Preparation of a HPTLC plate on the basis of silica gel 60 for linking to FTIR a) Preparation of the suspension 320 mL of water are admixed with 2.0 g of a high molecular weight acrylic acid (mean molecular weight $4 \times 10^6$), which are stirred in for 15 min at about 1200 rpm. The solution is admixed with 50 g of a silica gel 60 (mean particle size about 5 µm; grain size distribution 4–8 µm) customarily used in HPTLC, 50 g of a $Bi_2O_3$ powder (mean particle size about 4 µm) and 2.0 g of Mg tungstate (mean particle size about 3 µm), followed by stirring for a further 15 min at about 1200 rpm. Using 0.1N sodium hydroxide solution, the suspension is then set to a pH of 6.3, followed by stirring for a further 1 h at about 1200 rpm.

b) Coating of the glass plates

Glass plates of format 20×20 cm (glass thickness 1.25 mm) are coated as follows with the prepared suspension: A Desaga coater is charged with the suspension and passed across the glass plates, the knife being set to about 0.25 mm.

c) Drying

The coated glass plates are dried in a drying cupboard at about 110° C. for 30 min. The resulting layer thickness is about 100 µm.

Example 2

Separation of substances and ensuing linking to FTIR a) Separation of substances 5 µL of a solution, 0.02% strength in each case, of caffeine, paracetamol and phenazone in dichloromethane are sprayed onto the plate (using Linomat IV from CAMAG) in the form of bands (band length 3 mm). After drying the plate is developed in a normal chamber, without chamber saturation, with the mobile phase ethyl acetate/methanol 20/1 (v/v) to a migration distance of 4 cm and is then dried.

b) Recording of spectra

The measurements are carried out using an IFS48 FTIR spectrometer and the external DRIFT unit from Bruker. Evaluation is carried out via the spectrometer software OPUS Vers. 4.17 A.

Figure 2:
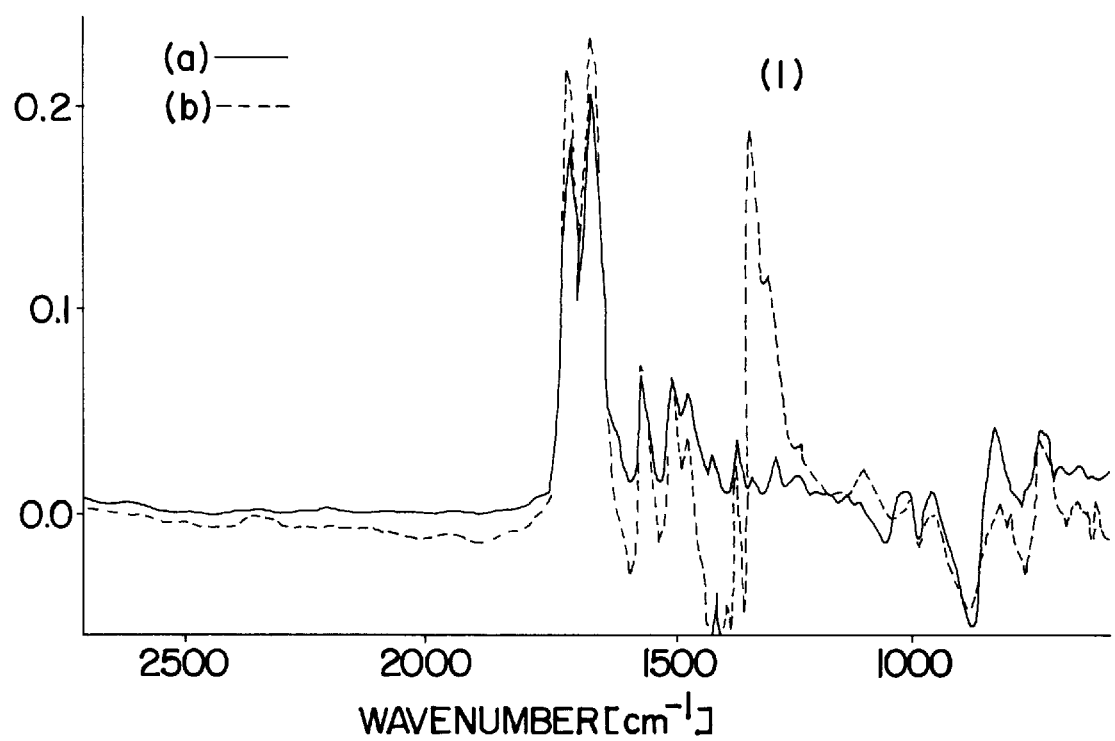
FIG. 2 shows the DRIFT spectrum, recorded in situ, of caffeine on a sorbent layer according to the invention, comprising 50% by weight of $Bi_2O_3$, compared with a layer without reflection enhancer.

The results are summarized in FIGS. 1 and 2:

FIG. 1 shows Gram-Schmidt chromatograms of phenazone (1), caffeine (2) and paracetamol (3) on a sorbent layer according to the invention, comprising 50% by weight of $Bi_2O_3$ (continuous line), compared with a layer without reflection enhancer (broken line).

FIG. 2 shows the DRIFT spectrum, recorded in situ, of caffeine on a sorbent layer according to the invention, comprising 50% by weight of $Bi_2O_3$ (continuous line), compared with a layer without reflection enhancer (broken line). (1) marks the position of the interfering band at wave number 1337 $cm^{-1}$, which occurs only in the comparative spectrum.

We claim:

1. A separating material for thin-layer chromatography which comprises, on a support, a sorbent layer comprising sorbent particles and at least 10 percent by weight, based on the weight of sorbent particles, of magnesium tungstate and/or $Bi_2O_3$ as a reflection enhancer.

2. The separating material according to claim 1, wherein the reflection enhancer is in the form of particles having a particle size of 2–20 µm.

3. The separating material according to claim 1, wherein the amount of the reflection enhancer is from 0.1 to 9 times the amount of the sorbent particles.

4. The separating material according to claim 1, wherein the sorbent particles comprise $SiO_2$.

5. The separating material according to claim 1, wherein the sorbent particles are hydrophobic reversed phase materials or hydrophilic materials modified with amino, cyano or diol groups.

6. The separating material according to claim 1, wherein the separating material further comprises a high molecular weight acrylic and/or methacrylic acid polymer as a binder.

7. The separating material according to claim 1, wherein the thickness of the sorbent layer is between 30 and 250 µm.

8. The separating material of claim 1, wherein the reflection enhancer is in the form of particles having a particle size of 3–5 µm.

9. The separating material of claim 1, wherein the amount of the reflection enhancer is from 0.6 to 1.5 times the amount of the sorbent particles.

10. A thin-layer chromatography method which comprises separating components of a composition on a separating material according to claim 1 and measuring, in situ, the FTIR spectrum thereof.

* * * * *